US012385017B2

(12) United States Patent
Mizushima

(10) Patent No.: US 12,385,017 B2
(45) Date of Patent: Aug. 12, 2025

(54) ACUTE RESPIRATORY DISTRESS SYNDROME THERAPEUTIC AGENT

(71) Applicant: LTT Bio-Pharma Co., Ltd., Tokyo (JP)

(72) Inventor: Toru Mizushima, Tokyo (JP)

(73) Assignee: LTT Bio-Pharma Co., Ltd., Tokyo (JP)

( * ) Notice: Subject to any disclaimer, the term of this patent is extended or adjusted under 35 U.S.C. 154(b) by 222 days.

(21) Appl. No.: 16/984,793

(22) Filed: Aug. 4, 2020

(65) Prior Publication Data

US 2020/0370025 A1 Nov. 26, 2020

Related U.S. Application Data

(62) Division of application No. 15/771,874, filed as application No. PCT/JP2016/079399 on Oct. 4, 2016, now abandoned.

(30) Foreign Application Priority Data

Oct. 29, 2015 (JP) ................. 2015-212824

(51) Int. Cl.
| | |
|---|---|
| C12N 9/02 | (2006.01) |
| A61K 9/00 | (2006.01) |
| A61K 38/44 | (2006.01) |
| A61K 47/26 | (2006.01) |
| A61P 11/00 | (2006.01) |

(52) U.S. Cl.
CPC .......... *C12N 9/0089* (2013.01); *A61K 9/0019* (2013.01); *A61K 9/0075* (2013.01); *A61K 9/0078* (2013.01); *A61K 38/44* (2013.01); *A61K 38/446* (2013.01); *A61K 47/26* (2013.01); *A61P 11/00* (2018.01); *C12Y 115/01001* (2013.01)

(58) Field of Classification Search
None
See application file for complete search history.

(56) References Cited

U.S. PATENT DOCUMENTS

| | | | | |
|---|---|---|---|---|
| 2010/0143321 A1* | 6/2010 | Shirai | ................... | A61K 47/544 424/94.3 |
| 2011/0262420 A1* | 10/2011 | Mizushima | .......... | A61K 47/186 424/94.4 |
| 2012/0034202 A1* | 2/2012 | Mizushima | .......... | A61K 9/0019 424/94.3 |
| 2013/0052154 A1 | 2/2013 | Kabanov et al. | | |
| 2016/0303099 A1* | 10/2016 | Dufu | ................... | C07D 403/04 |

FOREIGN PATENT DOCUMENTS

| | | |
|---|---|---|
| CN | 102238958 A | 11/2011 |
| CN | 102348465 A | 2/2012 |
| EP | 1 188 445 A1 | 3/2002 |
| JP | 9-117279 A | 5/1997 |
| JP | 2001-64199 A | 3/2001 |
| JP | 2010-215527 A | 9/2010 |
| WO | WO 2008/075706 A1 | 6/2008 |
| WO | WO 2010/064522 A1 | 6/2010 |

OTHER PUBLICATIONS

Jih, Thomas. Acute Respiratory Distress Syndrome (ARDS) and Severe Acute Respiratory Syndrome (SARS): Are We Speaking Different Languages? Elsevier. Journal of Chinese Medicine Assoc . Jan. 2005 . Vol 68 . No 1 (Year: 2005).*
Miyahara, Takashige et al. Lecithinized superoxide dismutase attenuates phorbol myristate acetate-induced injury in isolated dog lung. Elsevier. European Journal of Pharmacology 344 (1998). pp. 231-239. (Year: 1998).*
Gourd, Nicholas et al. Multiple Organ Dysfunction Syndrome. Journal of Intensive Care Medicine. 2020, vol. 35(12) 1564-1575. (Year: 2020).*
Marzi I., et al., "Value of Superoxide Dismutase for Prevention of Multiple Organ Failure After Multiple Trauma", The Journal of Trauma, 1993, pp. 110-120, vol. 35, No. 1 (11 pages).
Chinese-language Office Action issued in Chinese Application No. 201680063143.4 dated Sep. 27, 2021 with English translation (13 pages).
Japanese-language Office Action issued in Japanese Application No. 2020-214217 dated Nov. 24, 2021 with English translation (6 pages).
International Search Report (PCT/ISA/210) issued in PCT Application No. PCT/JP2016/079399 dated Nov. 8, 2016 with English translation (six pages).
Japanese-language Written Opinion (PCT/ISA/237) issued in PCT Application No. PCT/JP2016/079399 dated Nov. 8, 2016 (seven pages).
Fujino et al., "Assessment of Bleomyein-Induced Pulmonary Fibrosis by Bronchoalveolar Lavage", The Japanese Journal of Thoracic Diseases, 1989, pp. 180-187, vol. 27, No. 2 with English abstract and partial English translation.
Tokumine et al., "Kotsuzui Kansaibo Inyuni yoru Hai Shogai Shufuku Sokushin no Kokoromi", Respiratory Molecular Medicine, 2006, pp. 209-211, vol. 10, No. 3 with partial English translation.
Matute-Bello et al., "Animal models of acute lung injury" , American Journal of Physiology, Lung Cellular and Molecular Physiology, Jul. 11, 2008, pp. L379-L399, vol. 295, No. 3.
Yen et al., "Aerosolized Human Extracellular Superoxide Dismutase Prevents Hyperoxia-Induced Lung Injury", PLoS One, Oct. 26, 2011, pp. 1-9, vol. 6, No. 10.

(Continued)

*Primary Examiner* — Nghi V Nguyen
(74) *Attorney, Agent, or Firm* — Crowell & Moring LLP

(57) ABSTRACT

An agent for treating acute respiratory distress syndrome includes, as an active ingredient, a lecithinized superoxide dismutase represented by the general formula (I):

$$SOD'(Q\text{-}B)_m \qquad (I)$$

(wherein, SOD' represents a residue of a superoxide dismutase; Q represents a chemical crosslinking; B represents a residue of lysolecithin, in which a hydrogen atom of a hydroxyl group is removed from the lysolecithin having the hydroxyl group at the 2-position of glycerol; and m is the average number of bonds of the lysolecithin relative to one molecule of the superoxide dismutase and represents an integer of 1 or more).

10 Claims, 14 Drawing Sheets

(56) References Cited

OTHER PUBLICATIONS

Liu et al., "Superoxide Anion, the Main Species of ROS in the Development of ARDS Induced by Oleic Acid", Free Radical Research, Dec. 2004, pp. 1281-1287 (eight pages total), vol. 38, No. 12.
Koyama et al., "Recombinant-human Superoxide Dismutase Attenuates Endotoxin-induced Lung Injury in Awake Sheep", American Review of Respiratory Disease, 1992, pp. 1404-1409, vol. 145, No. 6.
Mizushima, "Development of Lecithinized Superoxide Dismutase as a Drug for IPF", Drug Delivery System, 2013, pp. 221-228, vol. 28, No. 3 with partial English translation.
Mizushima, "Lecithinized SOD no Rinsho Oyo", Respiratory Molecular Medicine, 2012, pp. 88-90, vol. 16, No. 1 with partial English translation.
Mizushima, "Development of Lecithinized Superoxide Dismutase as a Drug for IPF", The Pharmaceutical Society of Japan, 2014, pp. 69-76, vol. 134, No. 1 with partial English translation.
Hashimoto et al., "Lecithinized SOD no LPS Jakki Kyusei Hai Shogai ni Taisuru Keigen Koka ni Tsuite no Kento", The Japanese Journal of Thoracic Diseases, Mar. 1996, pp. 374 (two pages total), vol. 34 with partial English translation.
Yamada et al., "Jikken Koza ARDS Model Sakuseiho", Surgery Frontier, 2003, pp. 295-299, vol. 10, No. 3 with partial English translation.
Korean-language Office Action Issued In Korean Application No. 10-2018-7014931 dated Feb. 15, 2024 with English translation (12 pages).
Igarashi, R. et al., "Lecithinization of superoxide dismutase potentiates its protective effect against Forssman antiserum-induced elevation in guinea pig airway resistance", Journal of Pharmacology and Experimental Therapeutics, Sep. 1992, pp. 1214-1219, vol. 262, No. 3 (4 pages).
Medical Information of Seoul National University Hospital, "acute respiratory distress syndrome, ARDS", URL: http://www.snuh.org/health/nMedInfo/nView.do?category=DIS&medid=AA000602, Feb. 2024, with English translation (11 pages).

\* cited by examiner

[Figure 1]
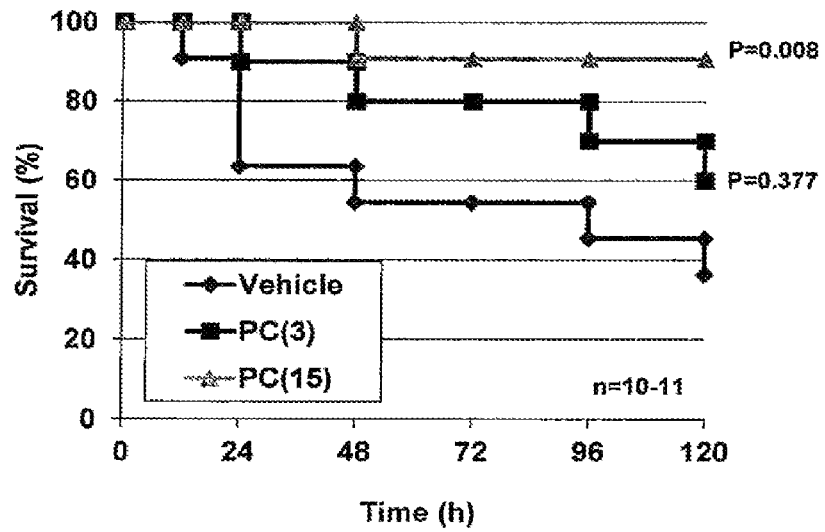
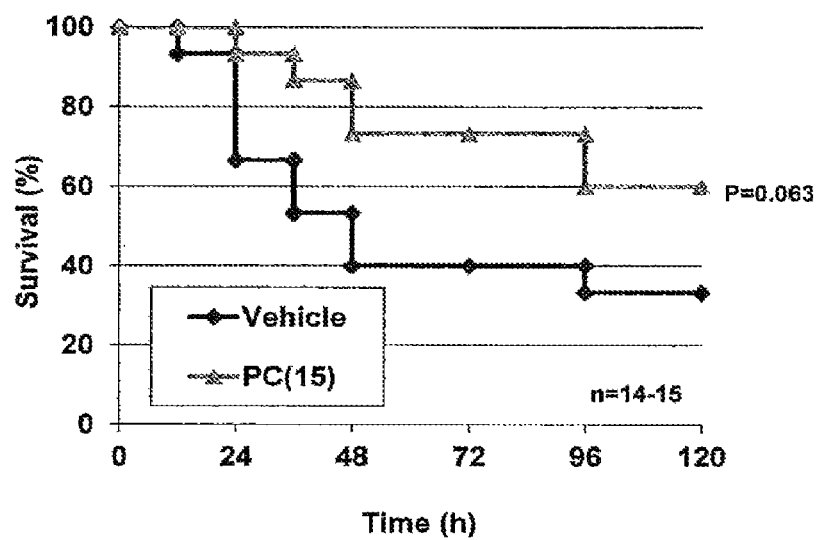

【Figure 2】
A
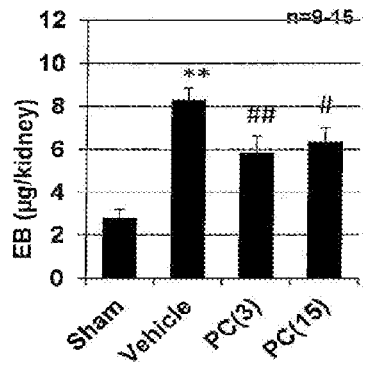 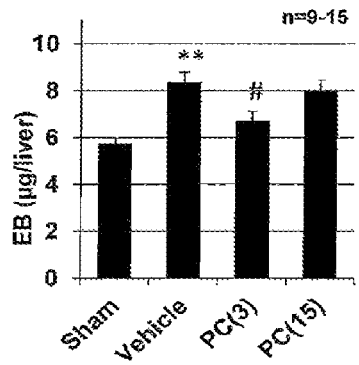
B
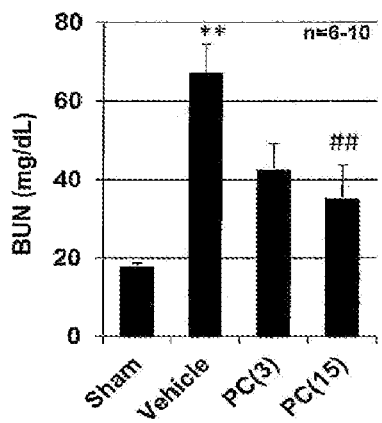 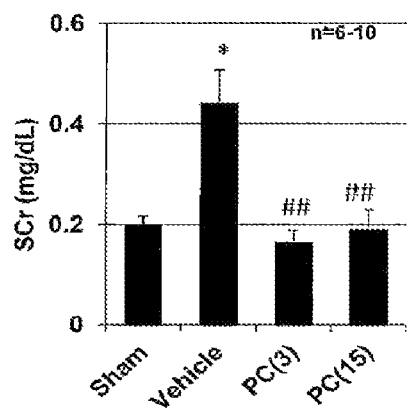
C 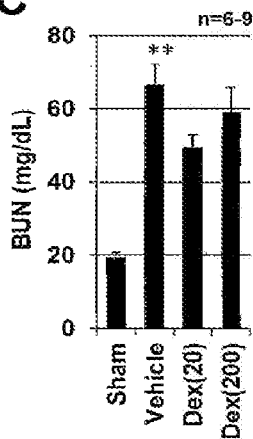 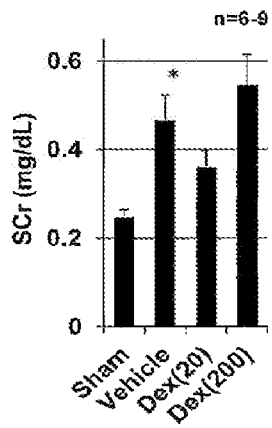 D 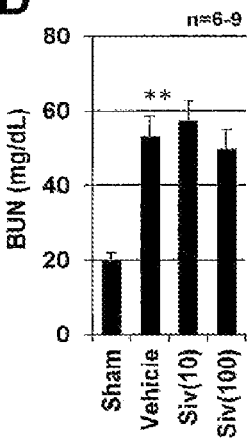 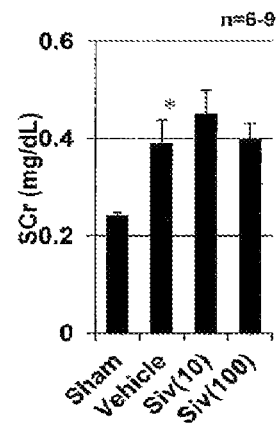

【Figure 3】
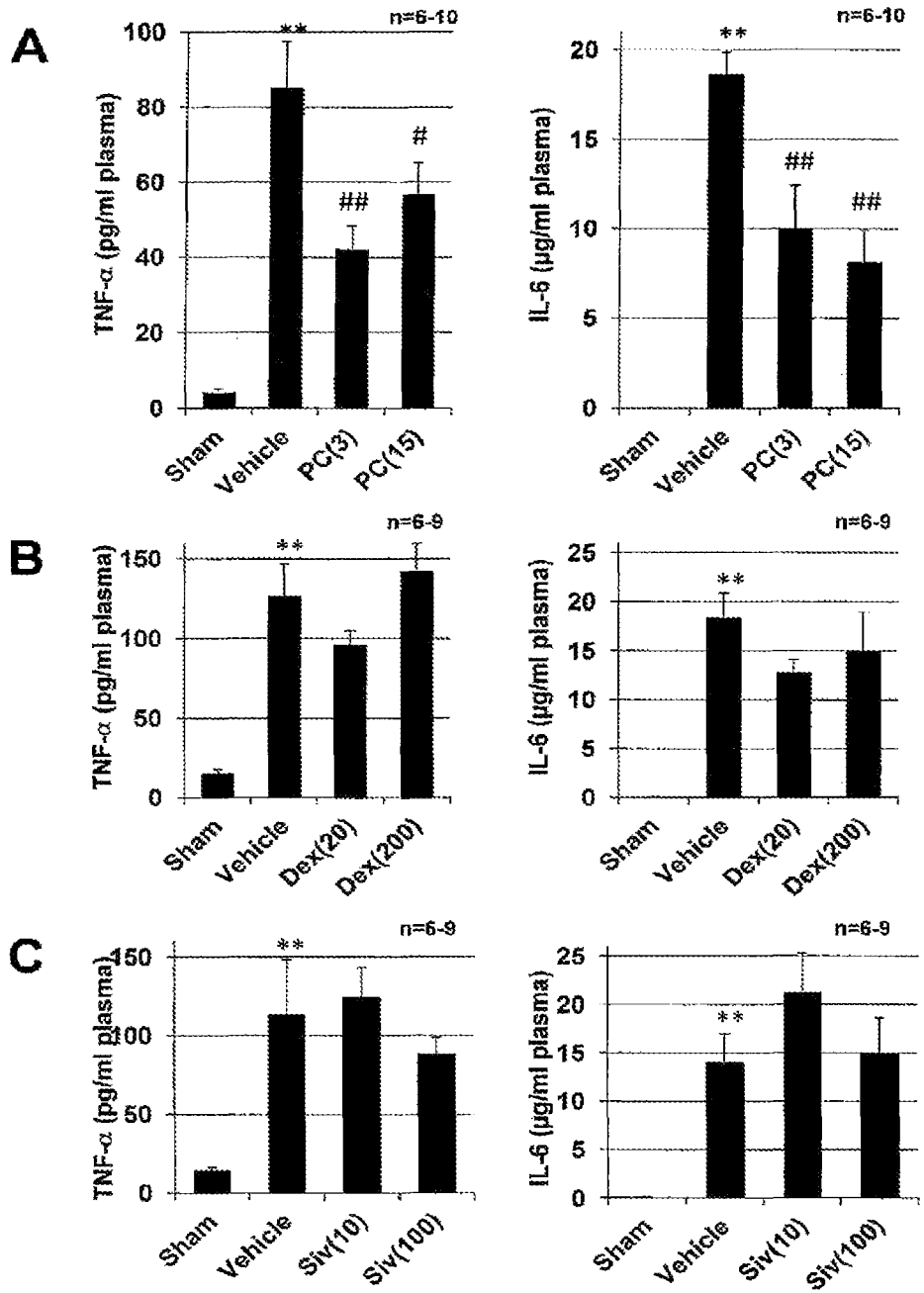

【Figure 4.1】
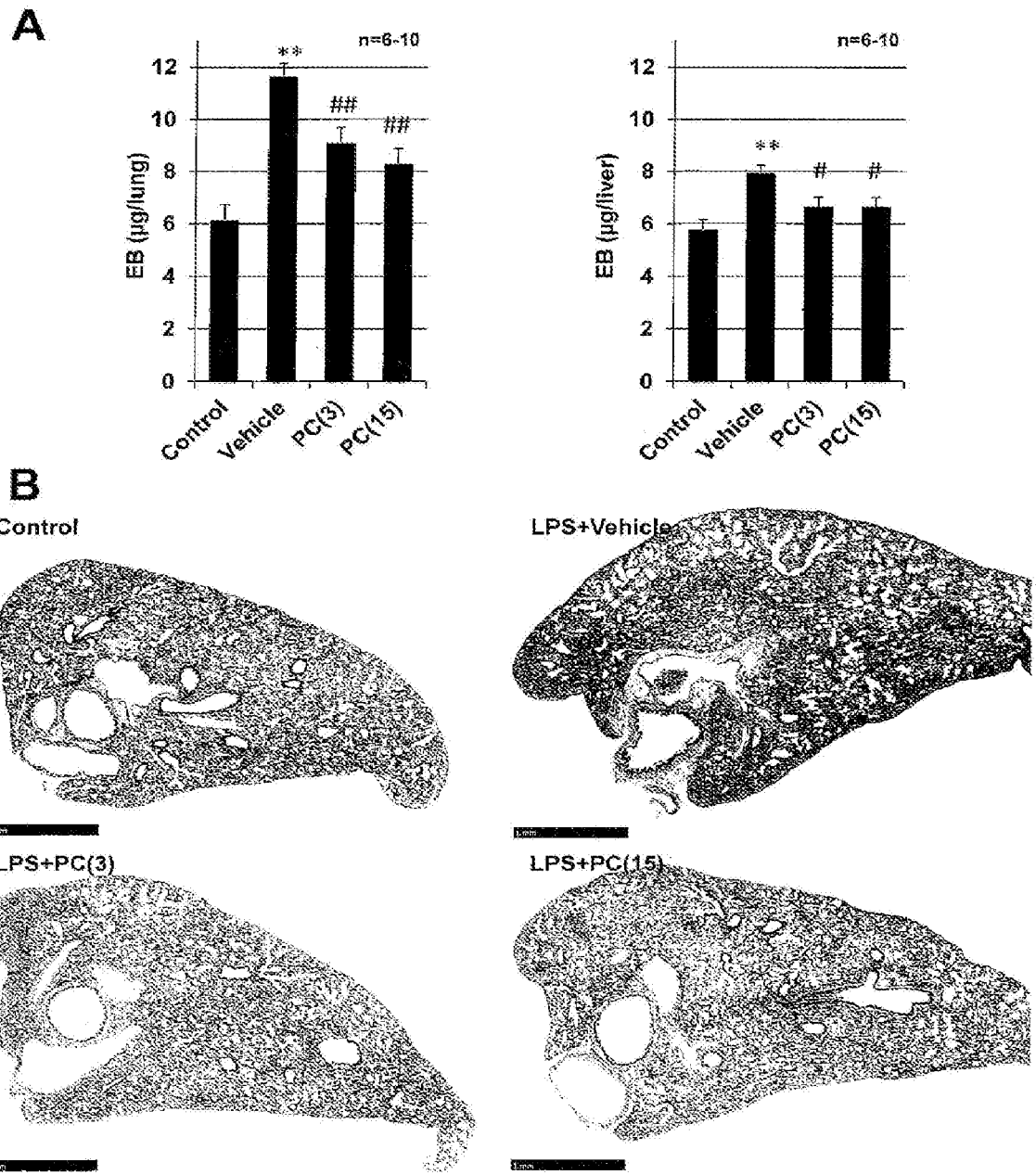

【Figure 4.2】
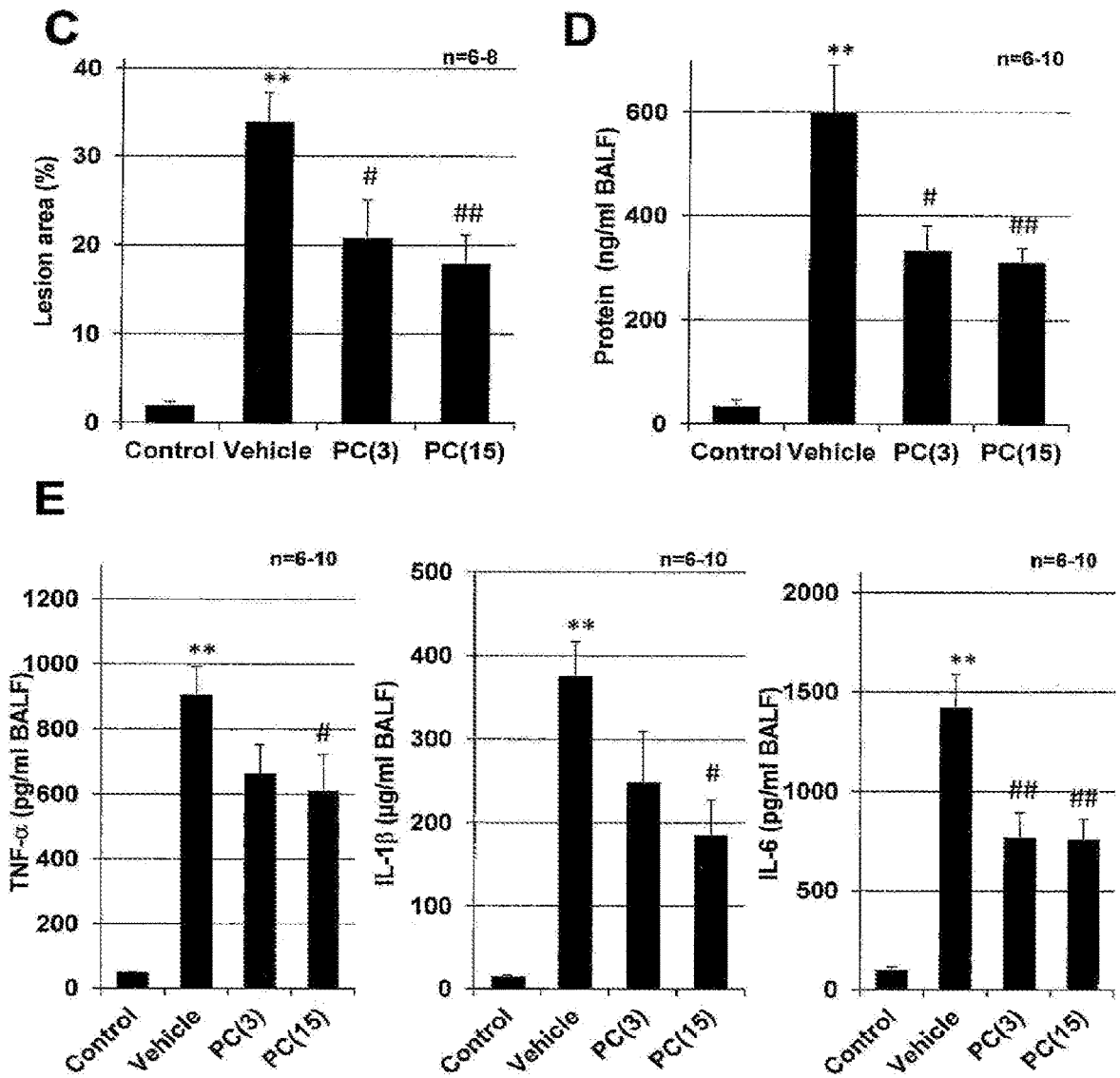

【Figure 5.1】
A
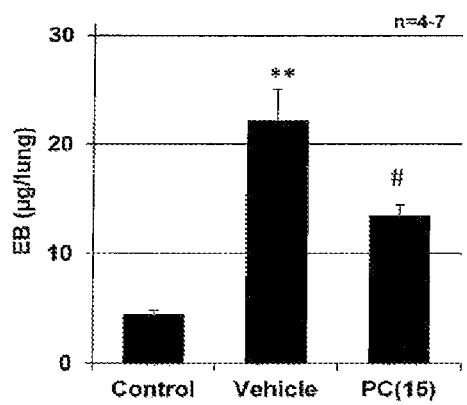
B
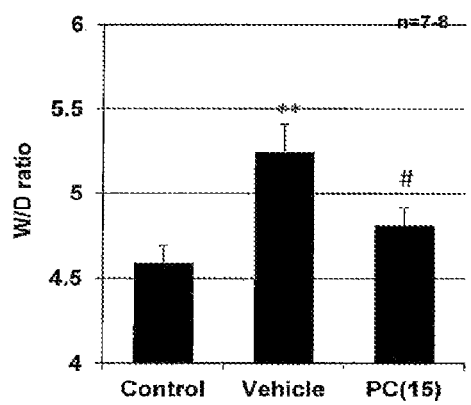
C
Ventilation+Vehicle
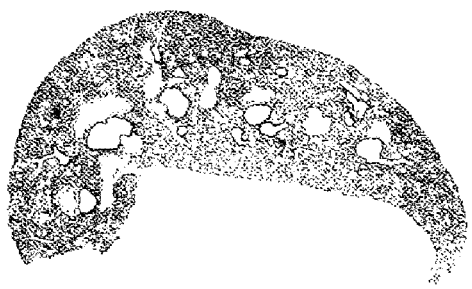
Ventilation + PC(15)
D
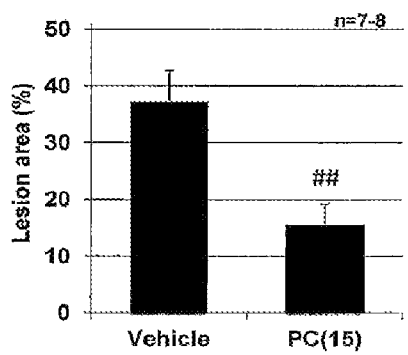

【Figure 5.2】
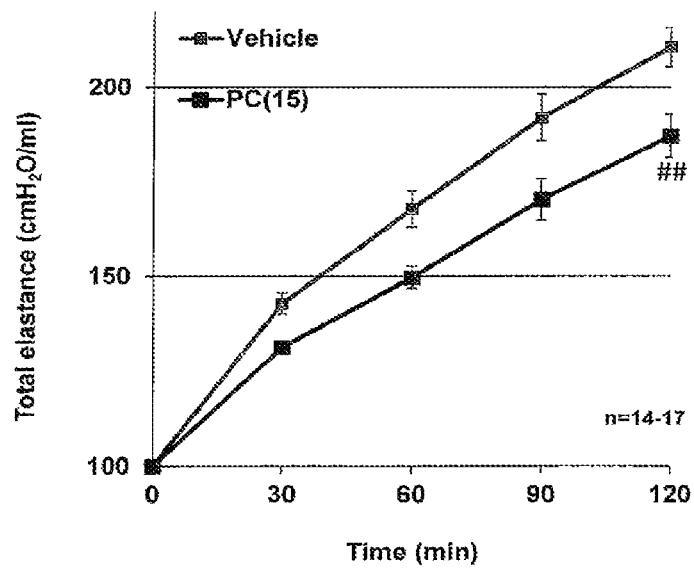

[Figure 6]
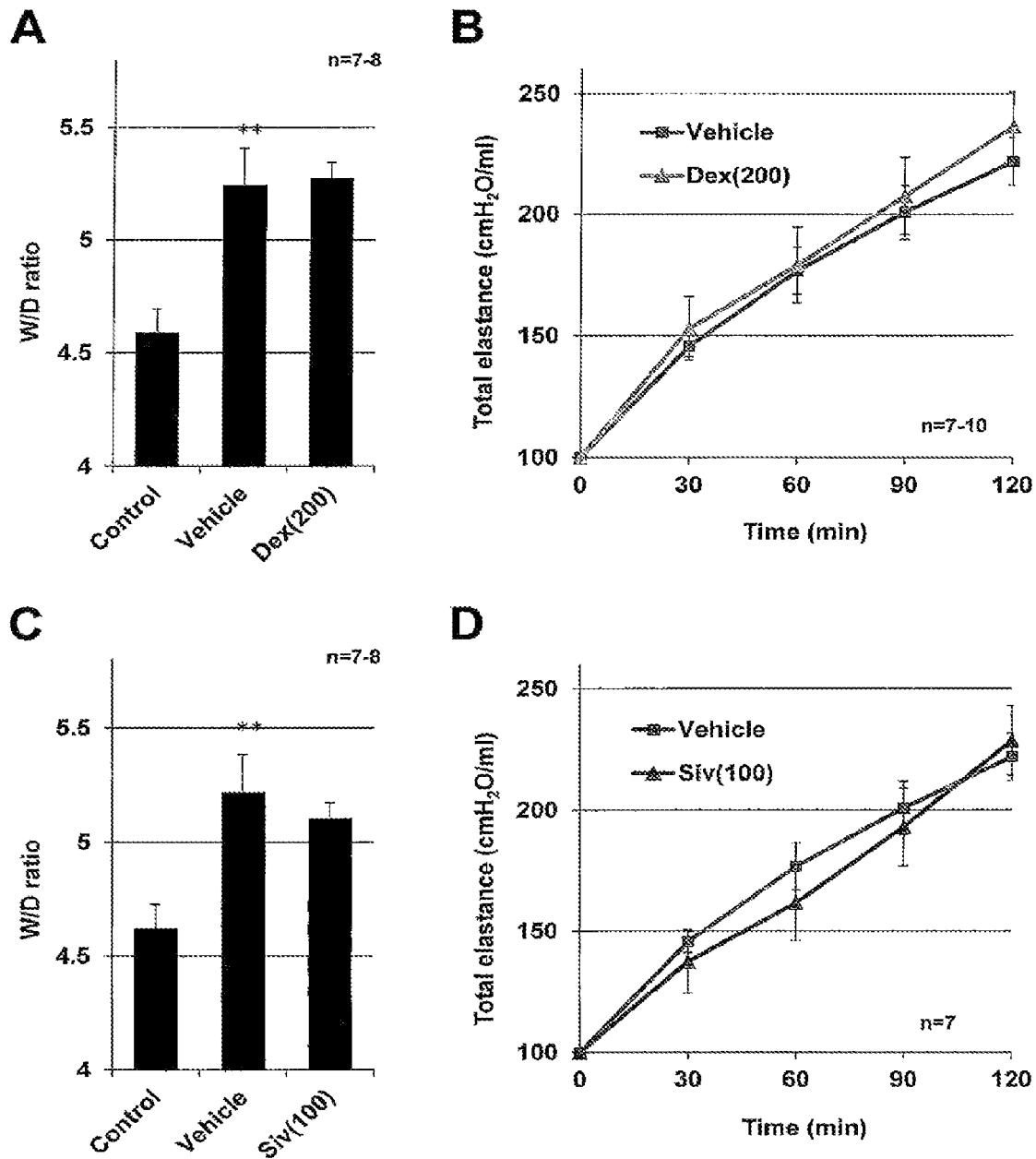

【Figure 7.1】
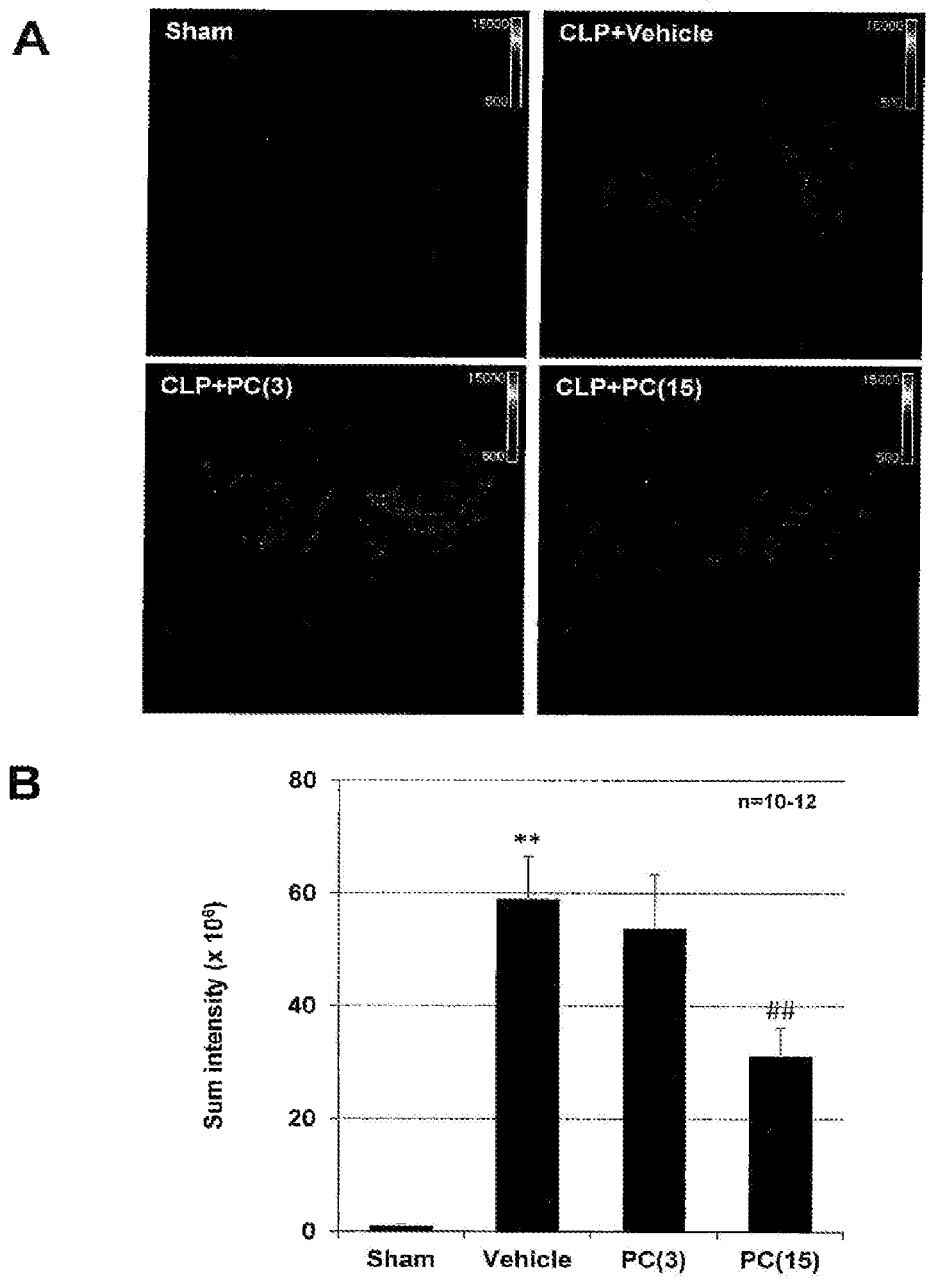

[Figure 7.2]
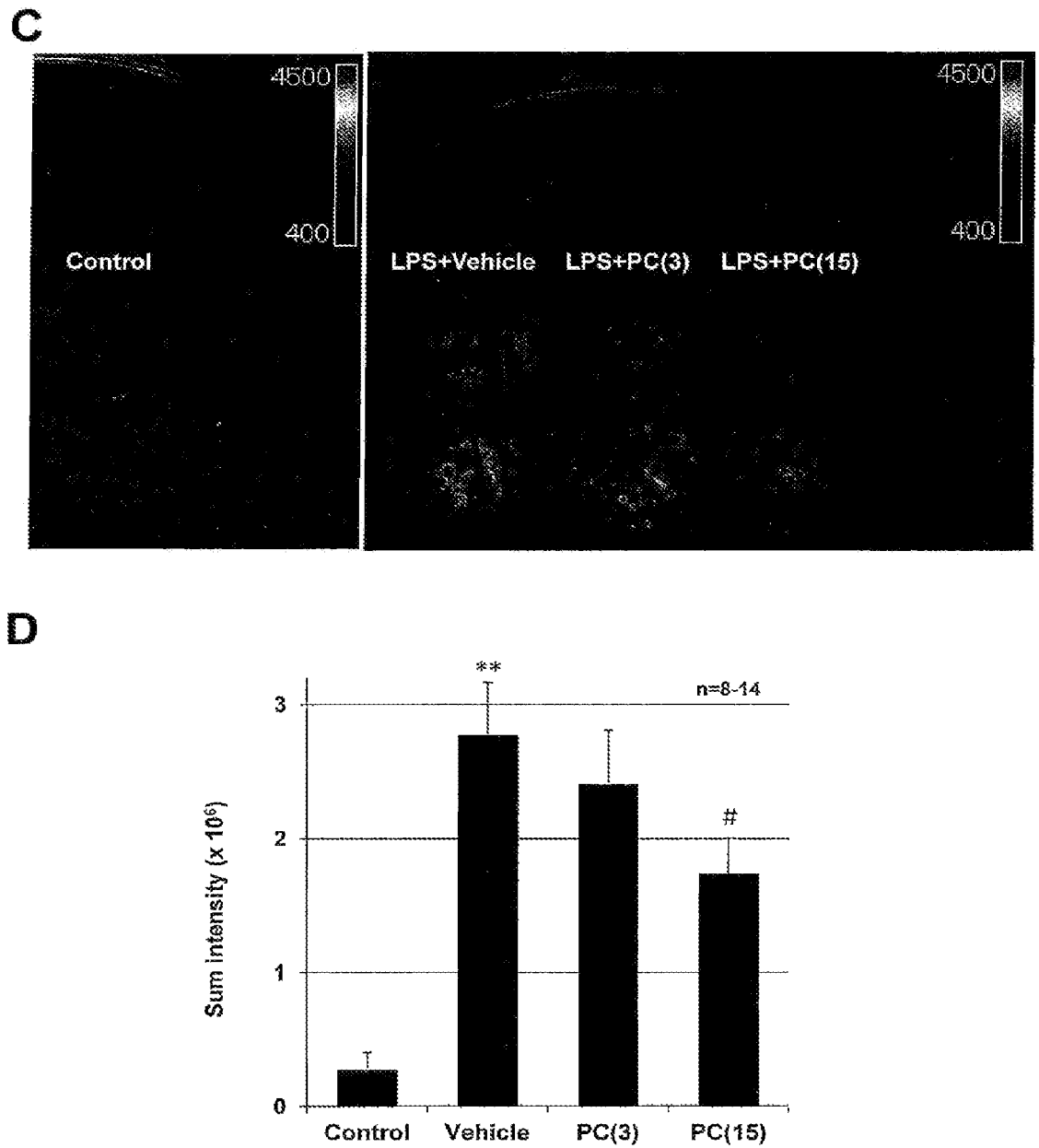

【Figure 7.3】
E
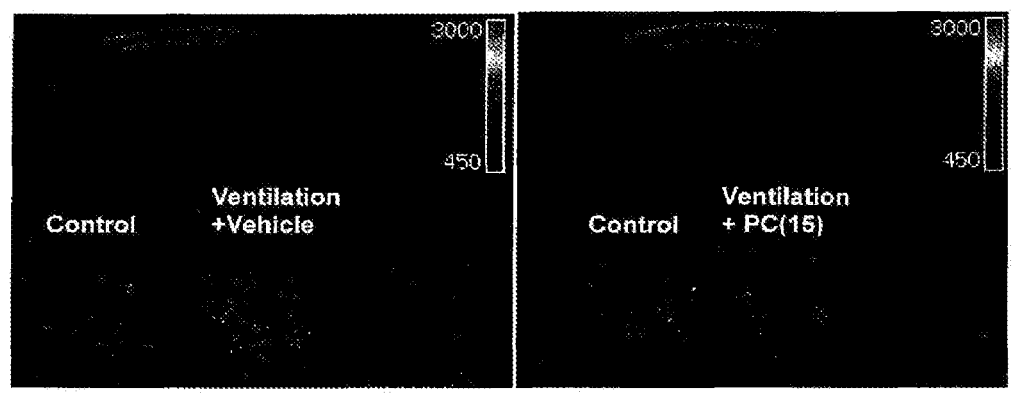
F
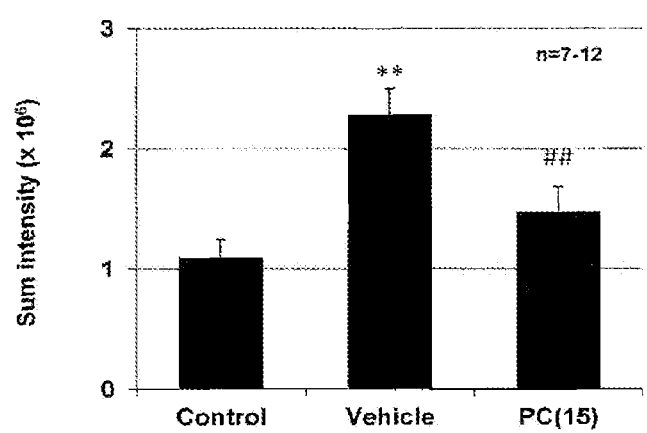

[Figure 8]
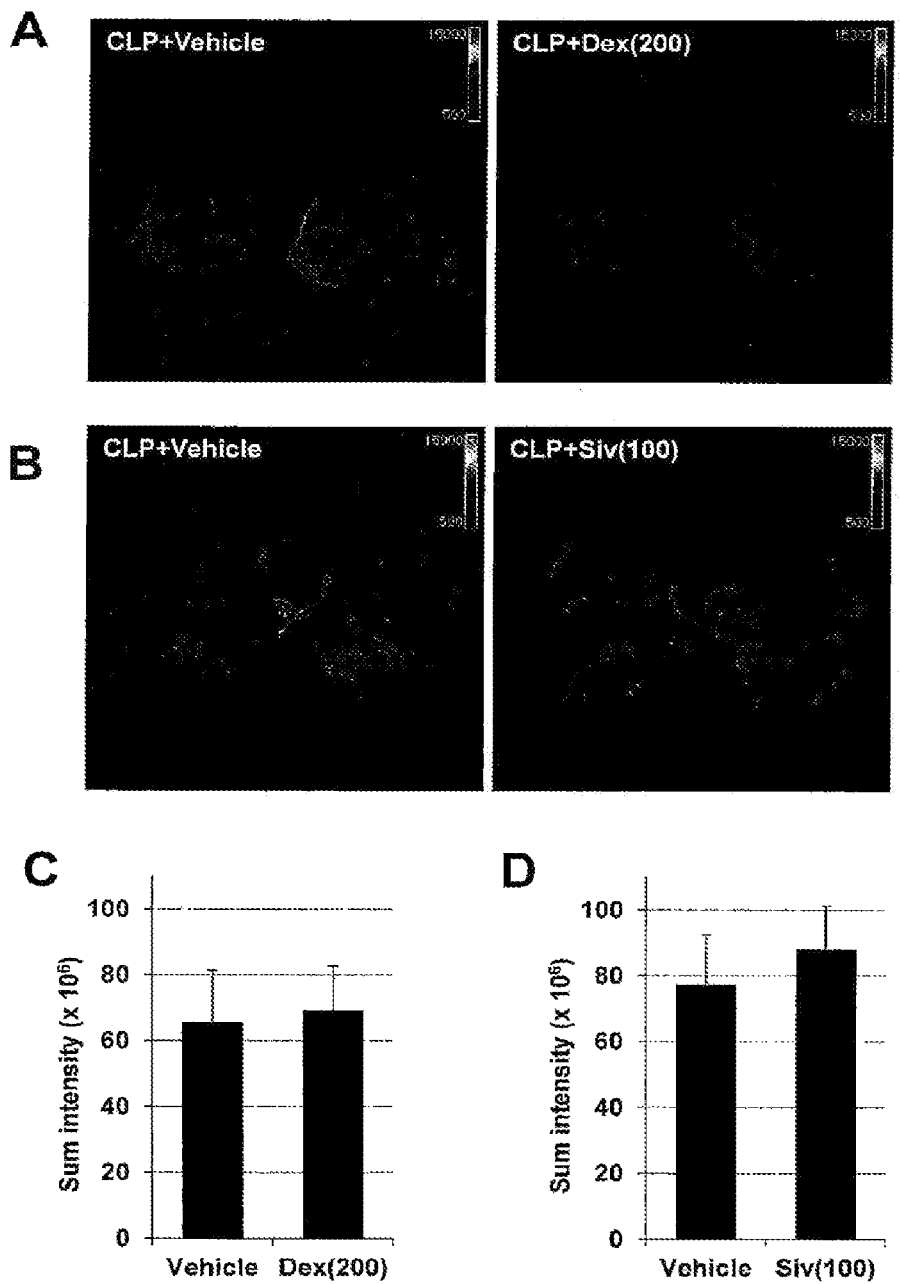

[Figure 9]
A
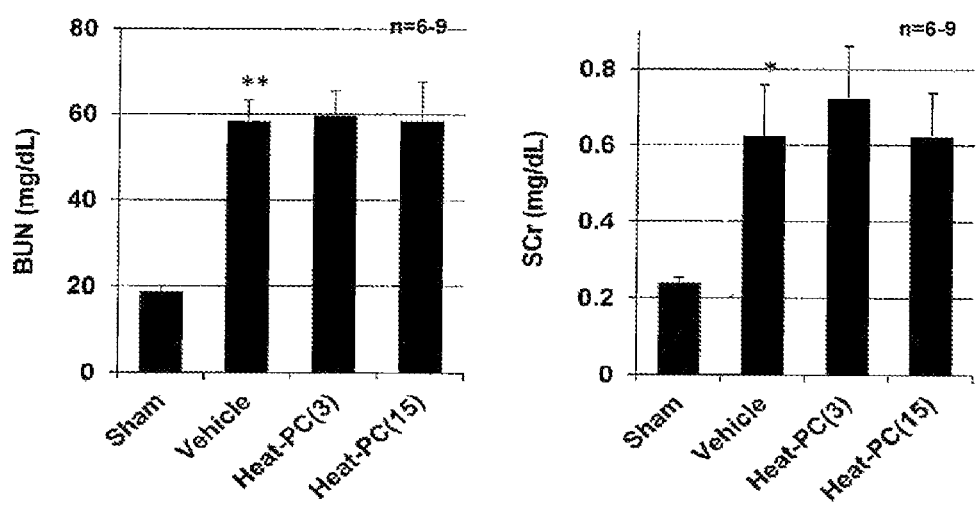
B
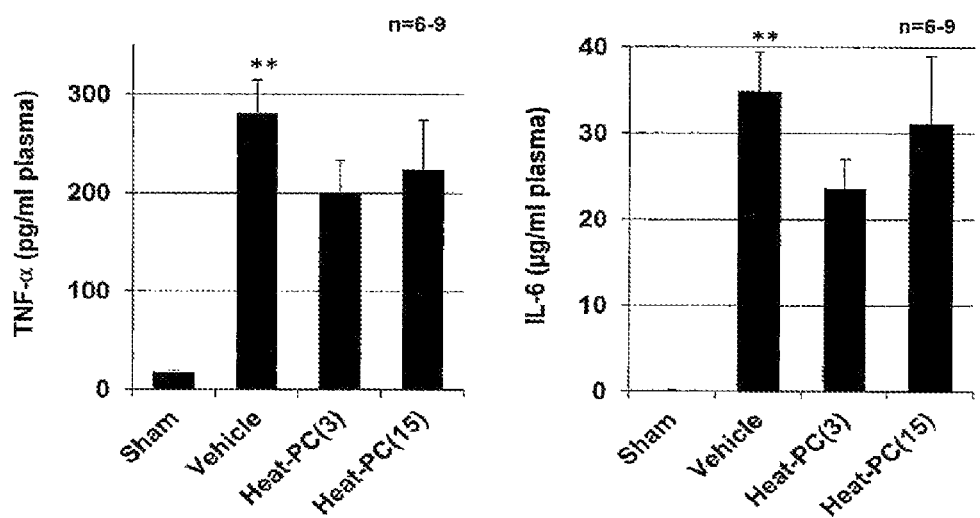

[Figure 10]
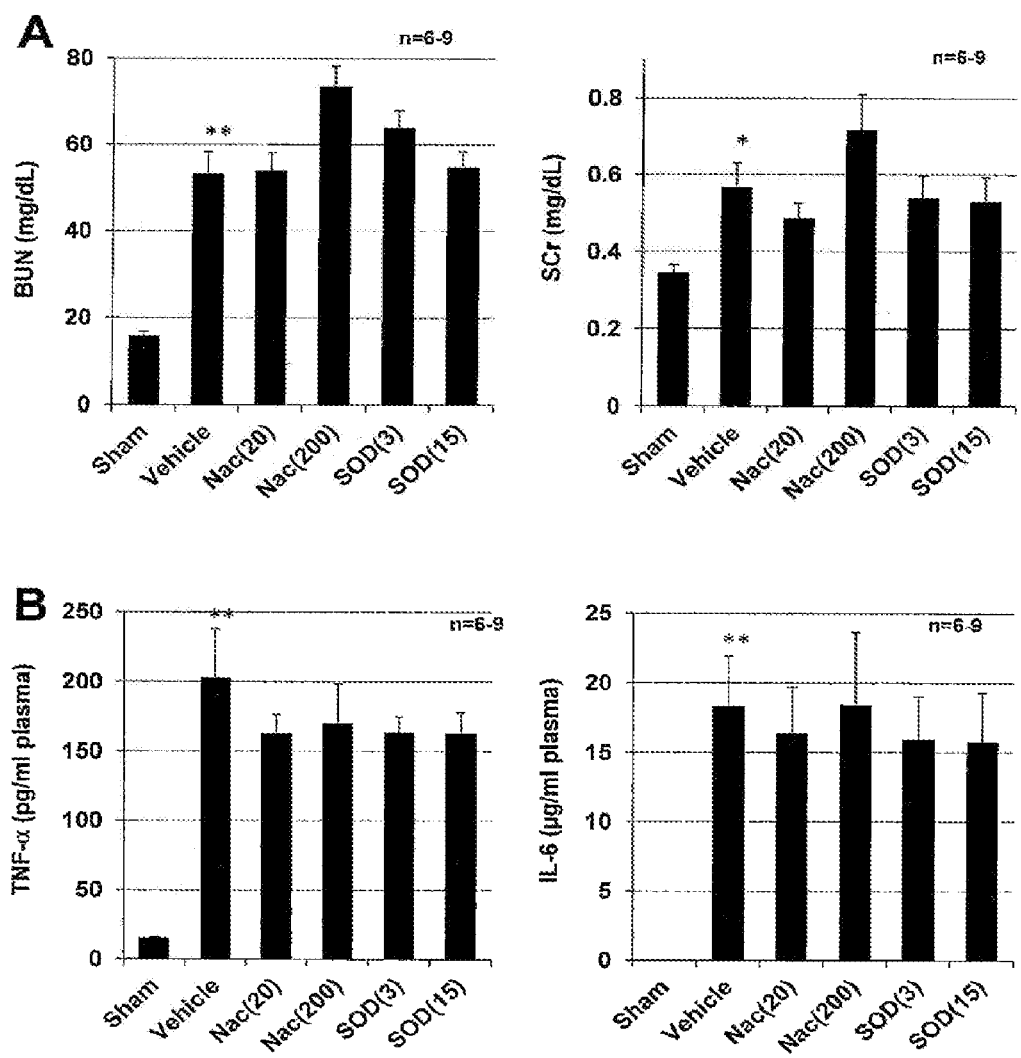

ACUTE RESPIRATORY DISTRESS SYNDROME THERAPEUTIC AGENT

CROSS REFERENCE TO RELATED APPLICATIONS

This application is a divisional of U.S. application Ser. No. 15/771,874, filed Apr. 27, 2018, which is a 371 of International Application No. PCT/JP2016/079399, filed Oct. 4, 2016, which claims priority from Japanese Patent Application No. 2015-212824, filed Oct. 29, 2015, the disclosures of which are expressly incorporated by reference herein.

TECHNICAL FIELD

The present invention relates to an agent for treating acute respiratory distress syndrome, and specifically, to an agent for treating acute respiratory distress syndrome that contains lecithinized superoxide dismutase (hereinafter may be referred to as "PC-SOD") as an active ingredient.

BACKGROUND ART

Acute respiratory distress syndrome (ARDS) (hereinafter may be referred to as "ARDS") is designated as "Kyuusei kokyuu sokuhaku shokogun" or "Kyuusei kokyuu kyuuhaku shokogun" in Japanese. This syndrome is one of the main causes of death among patients during intensive care and is a disease of great significance for public health. The annual number of ARDS patients has reached 200,000 in the United States. A reliable method for treating this disease has not been established yet and currently the mortality rate of ARDS is fairly high (40 to 50%).

ARDS is a fatal clinical syndrome defined by edema, acute hypoxic respiratory failure with cardiac filling pressure, and bilateral pulmonary infiltration. ARDS is sometimes associated with sepsis and pneumonia characterized by an injury of an alveolar capillary wall, in which edema fluid containing abundant protein leaks into a pulmonary alveolus, leading to reduced surfactant activity and increased lung elastance.

The injury of an epithelium and an endothelium also induces serious inflammatory response (for example, recruitment and activation of a leukocyte and production of an inflammatory cytokine precursor), increases vascular permeability (edema), and activates a coagulation system in all tissues as well as in the lung, resulting in a multifunctional failure.

ARDS is a disease that suddenly happens to a patient severely-ill due to sepsis, massive blood transfusion, severe pneumonia, a chest injury, pulmonary embolism, mechanical ventilation, pure oxygen inhalation, acute pancreatitis, or the like. Although the early-stage pathophysiology of ARDS is various, the processes leading to the eventual onset is mostly same.

In a patient having such a background, a tumor necrosis factor (TNF), interleukin-1 (IL-1), IL-6, IL-8, and the like are released into bloodstream. Since the lung is an organ through which blood circulating within a body always passes, the lung is susceptible to influence of the blood. Specifically, a neutrophil is attracted and releases reactive oxygen species and a protease in the lung tissue to injure, for example, an alveolar capillary epithelium and an alveolar epithelial tissue. The neutrophil that settled in the lung further releases, for example, G-CSF and GM-CSF to amplify local inflammation. This leads to an increase in vascular permeability and bloody exudate fills the interstitium and even the inside of the pulmonary alveolus.

Because of ventilation-perfusion mismatch and increased dead space, exhalation of $CO_2$ requires more ventilation than usual. However, reduction of lung compliance (lung consolidation) is caused in the early stage by the pulmonary alveolus filled with the exudate and in the late stage by the lung that underwent fibrosis, and consequently, mechanical ventilation at a high pressure becomes necessary.

Capillaries of the pulmonary alveolus constrict under poor ventilation and act to increase blood flow in a well-ventilated area. However, ventilation becomes poor in many areas of the lung in ARDS and therefore capillaries in these areas constrict to cause pulmonary hypertension.

It is reported that 15% of the patients in the intensive care unit (ICU) and 20% of the patients receiving mechanical ventilation develop ARDS.

Recently, a steroid has been used for treating ARDS, however, the effect thereof has not been proved yet. Although other various therapeutic approaches such as administration of a β-adrenergic agonist, activated protein C, or a statin drug are under investigation, the effects thereof are very restricted.

Furthermore, although a mechanical ventilator (MV: mechanical ventilation) (hereinafter may be referred to as "MV") is important for critical care for an ARDS patient, MV involves a high tidal volume and repeated gas flow by forced ventilation, causing ventilator-induced lung injury (VILI). This VILI increases the mortality rate of ARDS patients.

For this reason, MV with a low tidal volume is clinically recommended; however, a recent research states that even MV with a low tidal volume causes VILI and alveolar injury.

Therefore, it is also an important issue to suppress not only ARDS but also VILI for increasing the survival rate of ARDS patients.

Reactive oxygen species (ROS) (hereinafter may be referred to as "ROS") play an important role in damaging the lung in VILI as well as ARDS. In the ARDS patient, ROS are produced highly in an infiltrating leukocyte and under a high oxygen environment created by the mechanical ventilator. The mechanical ventilator also stimulates production of reactive oxygen species by extending the lung tissue excessively. ROS directly or indirectly induce inflammatory response, that is, activate inflammatory reaction in the lung and other organs to induce vascular permeability and activation of the coagulation system. In the ARDS patient and the patient on the mechanical ventilator, the level of reactive oxygen species (ROS), for example, a superoxide anion is reported to be elevated in blood plasma, exhaled breath condensate, and broncholveolar lavage fluid (BALF). This elevation in the level of reactive oxygen species is also observed in a model animal such as a peritonitis model generated by a cecal ligation and puncture technique (CLP technique) (hereinafter may be referred to as "CLP"), an animal that received lipopolysaccharide (LPS) (hereinafter may be referred to as "LPS"), or an animal having an MV-induced tissue damage (mechanical ventilator-induced tissue damage) in the lung.

Sivelestat (sivelestat sodium hydrate) is a neutrophil elastase inhibitor and is a drug used for ARDS patients in Japan. Neutrophil elastase is a protease produced by a neutrophil and the neutrophil elastase inhibitor prevents acute lung injury in an animal model. However, the clinical effect of sivelestat is not necessarily satisfactory. For example, administration of sivelestat did not decrease the mortality rate of ARDS patients.

This suggests that this is because sivelestat is not directly effective in suppressing ROS production and therefore indicates that treatment of a tissue injury mediated by ROS in ARDS cannot be achieved clinically by sivelestat.

On the other hand, an antioxidative function is operative in a living body. For example, catalase, which exists in a peroxisome in a cell and performs oxidation and detoxification by using hydrogen peroxide; superoxide dismutase (SOD), an enzyme that decomposes reactive oxygen species generated in a cell; and glutathione peroxidase have an antioxidative function and this function counters an oxidizing system effectively.

SOD is an enzyme that eliminates a reactive oxygen anion, and so far an isozymic form of SOD such as Cu/Zn SOD, magnesium-SOD, or an extracellular (EC)-SOD has been found to exist. Reduction of the activity and production level of this kind of antioxidant enzyme is observed in the ARDS patient and the VILI patient, as well as the animal model.

Accordingly, these antioxidant enzymes may be an effective therapeutic drug for ARDS and there have been many clinical and nonclinical reports based on this idea.

For example, the lung function of the ARDS patient is improved in response to antioxidant therapy using N-acetylcysteine (NAC), and the occurrence of organ failure is reduced by taking an antioxidant supplement such as α-tocopherol or ascorbic acid. In these cases, the treatment period of the ARDS patient in the ICU treatment room (central treatment room) is shortened. Furthermore, there have been many reports on efficacy of this kind of antioxidant enzyme.

As for SOD, an isozymic (iso) form of SOD (Cu/Zn SOD) that is a genetically modified SOD derivative has been proposed and the clinical application thereof has been performed. However, the clinical application was unsuccessful since this Cu/Zn SOD has low tissue affinity and low stability in blood plasma.

In view of these facts, the present inventors have developed lecithinized SOD (PC-SOD) (Patent Literatures 1 and 2). The PC-SOD is a lecithinized SOD obtained by preparing a human Cu/Zn-superoxide dismutase (SOD) by gene recombination technology, and then chemically binding an average of four molecules of lecithin derivative (phosphatidylcholine derivative: PC) relative to one molecule of SOD (dimer).

Then, the present inventors have confirmed that administration of PC-SOD is clinically effective against a disease such as ulcerative colitis or idiopathic pulmonary fibrosis (IPF).

Furthermore, the present inventors have developed an inhalation (inhalant) of the PC-SOD and have confirmed, albeit confirmation at the animal level, that the inhalation was effective against bleomycin-induced pulmonary fibrosis, elastase-induced, and smoking-induced pneumonia, as well as pulmonary emphysema (chronic obstructive pulmonary disease: COPD) (Patent Literature 3).

The above-mentioned chronic obstructive pulmonary disease (COPD) is a disease affecting a bronchus and a pulmonary alveolus caused by continuous airflow limitation on a respiratory tract and is characterized by a disrupted alveolar wall and an enlarged trachea. The etiological factor of COPD is basically different from that of ARDS.

Herein, the present inventors evaluated an effect of PC-SOD on ARDS and VILI. Consequently, the present inventors have confirmed that PC-SOD was effective against edema, tissue injury, and inflammation in the lung and other organs that neither the steroid nor sivelestat was effective against, and have found that PC-SOD could be a therapeutic drug for ARDS and VILI.

PRIOR ART DOCUMENTS

Patent Literature

Patent Literature 1: Japanese Patent Application Laid-Open No. Hei 9-117279
Patent Literature 2: Japanese Patent Application Laid-Open No. 2001-64199
Patent Literature 3: International Publication No. WO 2010/64522

SUMMARY OF THE INVENTION

Problems to be Solved by the Invention

Therefore, in view of the above-described present circumstances, it is an object of the present invention to provide an agent for treating ARDS (acute respiratory distress syndrome), and in particular, an agent for treating acute respiratory distress syndrome containing lecithinized superoxide dismutase (PC-SOD) as an active ingredient.

Means for Solving the Problem

Specifically, an aspect of the present invention is:
(1) an agent for treating acute respiratory distress syndrome including, as an active ingredient, a lecithinized superoxide dismutase represented by the following general formula (I):

$$SOD'(Q-B)_m \qquad (I)$$

(wherein, SOD' represents a residue of a superoxide dismutase; Q represents a chemical crosslinking; B represents a residue of lysolecithin, in which a hydrogen atom of a hydroxyl group is removed from the lysolecithin having the hydroxyl group at the 2-position of glycerol; and m is an average number of bonds of the lysolecithin relative to one molecule of the superoxide dismutase and represents an integer of 1 or more).

More specifically, the present invention includes the following aspects:
(2) the agent for treating acute respiratory distress syndrome according to the aspect (1) as described above, wherein Q in the general formula (I) is —C(O)—(CH$_2$)$_n$C(O)— (wherein, n represents an integer of 2 or more);
(3) the agent for treating acute respiratory distress syndrome according to the aspect (1) or (2) as described above, wherein SOD' is a residue of a human superoxide dismutase;
(4) the agent for treating acute respiratory distress syndrome according to the aspect (1) or (2) as described above, wherein SOD' is a residue of a modified superoxide dismutase in which an amino acid at a 111-position in an amino acid sequence of a human superoxide dismutase is converted into S-(2-hydroxyethylthio) cysteine;
(5) the agent for treating acute respiratory distress syndrome according to the aspect (3) or (4) as described above, wherein the superoxide dismutase is a superoxide dismutase containing copper and zinc in an active center thereof;

(6) the agent for treating acute respiratory distress syndrome according to any one of the aspects (2) to (5) as described above, wherein n is an integer of 2 to 10;
(7) the agent for treating acute respiratory distress syndrome according to any one of the aspects (1) to (6) as described above, wherein m is an integer of 1 to 12;
(8) the agent for treating acute respiratory distress syndrome according to any one of the aspects (1) to (7) as described above, further including a stabilizing agent;
(9) the agent for treating acute respiratory distress syndrome according to the aspect (8) as described above, wherein the stabilizing agent is a sugar;
(10) the agent for treating acute respiratory distress syndrome according to the aspect (9) as described above, wherein the sugar is sucrose; and
(11) the agent for treating acute respiratory distress syndrome according to the aspect (1) as described above, wherein sucrose is sucrose treated with activated carbon.

Effects of the Invention

The present invention provides an agent for treating acute respiratory distress syndrome that contains PC-SOD as an active ingredient. This agent is effective against edema, tissue injury, and inflammation in the lung and other organs that neither the steroid nor sivelestat was effective against, and thus brings new hope to treatment of ARDS and VILI.

BRIEF DESCRIPTION OF DRAWINGS

FIG. 1 includes graphs showing the results of Test Example 1 (A and B: survival rate).
FIG. 2 includes graphs showing the results (A to D) of Test Example 2.
FIG. 3 includes graphs showing the results (A to C) of Test Example 3.
FIG. 4.1 includes diagrams showing the results (A, B) of Test Example 4.
FIG. 4.2 includes graphs showing the results (C to E) of Test Example 4.
FIG. 5.1 includes diagrams showing the results (A to D) of Test Example 5.
FIG. 5.2 is a graph showing the results (E) of Test Example 5.
FIG. 6 includes graphs showing the results (A to D) of Test Example 6.
FIG. 7.1 includes diagrams showing the results (A and B) of Test Example 7.
FIG. 7.2 includes diagrams showing the results (C and D) of Test Example 7.
FIG. 7.3 includes diagrams showing the results (E and F) of Test Example 7.
FIG. 8 includes diagrams showing the results (A to D) of Test Example 8.
FIG. 9 includes graphs showing the results (A and B) of Test Example 9.
FIG. 10 includes graphs showing the results (A and B) of Test Example 10.

EMBODIMENTS FOR CARRYING OUT THE INVENTION

With respect to the lecithinized superoxide dismutase (PC-SOD) used for the agent for treating acute respiratory distress syndrome provided by the present invention, the term "lecithin" refers to normal lecithin, which means phosphatidylcholine, and the term "lysolecithin" refers to a compound in which one molecule of fatty acid bound at the 2-position of glycerol in lecithin is removed and a hydroxyl group is bound to the carbon atom at the 2-position.

The PC-SOD used in the present invention can be usually obtained by binding one or more lecithin derivatives, in which a chemical crosslinking agent is bound to the hydroxyl group at the 2-position of lysolecithin, to the SOD. The PC-SOD can be represented by the following formula (I):

$$SOD'(Q\text{-}B)_m \qquad (I)$$

(wherein, SOD' represents a residue of the superoxide dismutase; Q represents a chemical crosslinking; B represents a residue of lysolecithin, in which a hydrogen atom of a hydroxyl group is removed from the lysolecithin having the hydroxyl group at the 2-position of glycerol; and m is the average number of bonds of the lysolecithin; and m is the average number of bonds of lysolecithin relative to one molecule of the superoxide dismutase and represents an integer of 1 or more).

The origin of SOD' used herein is not particularly limited as long as the SOD' can exert an essential function of decomposing reactive oxygen species ($O_2^-$) in a living organism. SOD residues derived from various plants, animals, or microorganisms can be widely used. However, in view of application of SOD' to medicines, it is preferable that antigenicity thereof in the living organism be reduced as much as possible. Accordingly, it is preferable to suitably select an appropriate SOD residue as an SOD' to be used, depending on a subject, to which the agent for treating acute respiratory distress syndrome of the present invention is administered.

For example, the SOD' is intended to be administered to an actual patient with acute respiratory distress syndrome as the subject. Therefore, in order to reduce antigenicity in the living organism due to the administration as much as possible, a human-derived SOD residue is preferably used. Accordingly, in view of antigenicity, the human-derived SOD may be used advantageously as the agent for treating acute respiratory distress syndrome of the present invention.

A human-derived Cu/Zn SOD (human-derived SOD containing copper and zinc in the active center; hereinafter may be abbreviated as human Cu/Zn SOD) is particularly preferably used as the human-derived SOD. This is because the human Cu/Zn SOD is expressed in a large amount in cells and the production technology therefor based on a genetic engineering method has been already established, whereby the human Cu/Zn SOD can be prepared in a large amount.

Examples of the human Cu/Zn SOD include: a natural human Cu/Zn SOD produced from human tissues or cultured cells; a human Cu/Zn SOD produced by the genetic engineering method; a recombinant human Cu/Zn SOD having substantially the same amino acid sequence as in the natural human Cu/Zn SOD; an SOD where some amino acids in the amino acid sequences of these human Cu/Zn SODs are deleted, added, substituted, or chemically modified or changed. Any human Cu/Zn SOD may be used.

Among them, a human Cu/Zn SOD in which an amino acid (cysteine: Cys) at the 111-position of the amino acid sequence of the natural human Cu/Zn SOD has been converted into S-(2-hydroxyethylthio)cysteine is preferable. Such a human Cu/Zn SOD is described in detail in, for example, Japanese Patent Application Laid-Open No. Hei. 9-117279, and can be obtained by the method described therein.

Accordingly, preparation of the human Cu/Zn SOD described in Japanese Patent Application Laid-Open No. Hei 9-117279 is partially incorporated herein, and the PC-SOD used in the present invention can be obtained by using these human Cu/Zn SODs as a material.

In the PC-SOD represented by the formula (I) used in the present invention, "a residue of lysolecithin, in which a hydrogen atom of a hydroxyl group is removed from the lysolecithin having the hydroxyl group at the 2-position of glycerol" shown as B is specifically represented by the following formula (II):

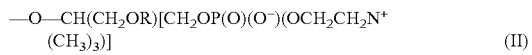

(wherein, R is a fatty acid residue (acyl group)).

The fatty acid residue (acyl group) represented by R is preferably a saturated or unsaturated fatty acid residue of 10 to 28 carbon atoms, more preferably a myristoyl group, a palmitoyl group, a stearoyl group, an icosanoyl group, a docosanoyl group, or other saturated fatty acid residues of 14 to 22 carbon atoms, and particularly preferably a palmitoyl group, which is a saturated fatty acid residue of 16 carbon atoms.

The chemical crosslinking represented by Q in the general formula (I) is not particularly limited as long as an SOD and lecithin can be crosslinked to be chemically (covalently) bound with each other. Such a chemical crosslinking is particularly preferably a residue:

—C(O)—(CH$_2$)$_n$—C(O)— (wherein, n represents an integer of 2 or more). This residue is a residue without hydroxyl groups at both the ends of a linear dicarboxylic acid represented by a formula: HO—C(O)—(CH$_2$)$_n$—C(O)—OH, an anhydride, ester, or halide thereof, or the like (provided that in the case of the anhydride, ester, and halide, moieties corresponding to the hydroxyl groups at both the ends are removed).

When Q in the general formula (I) is the above-described linear dicarboxylic acid residue, one end of Q is bound to oxygen atom derived from the hydroxyl group of the lysolecithin residue represented by the formula (II) through an ester bond. Further, the other end of Q whose one end has famed the ester bond is directly bound to an amino group of the SOD through an amide bond, or the like.

In the residue of the above-described chemical crosslinking, n is an integer of 2 or more, and preferably an integer of 2 to 10.

In the formula (I), m represents the average number of bonds of lysolecithin relative to one molecule of SOD. Accordingly, m is an integer of 1 or more, preferably 1 to 12, and particularly preferably 4.

A method for producing PC-SOD used in the present invention, that is, a method for binding a lecithin derivative with an SOD, and preferably with a human Cu/Zn SOD can be performed, for example, by using the method described in Japanese Patent Application Laid-Open No. Hei 9-117279.

The chemical structure of the preferable PC-SOD is schematically shown below and the following PC-SOD is particularly preferable.

[Chemical Formula 1]

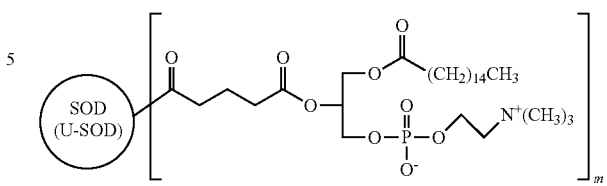

(wherein m is the number of bound lecithin derivatives).

In other words, the PC-SOD is obtained by covalently binding an average of four molecules of lecithin derivative to a free amino group of a human Cu/Zn SOD produced by genetic recombination using *E. coli* as a host cell.

It is preferable that the PC-SOD used in the agent for treating acute respiratory distress syndrome of the present invention be purified to such an extent that it is usable as a medicine and does not substantially contain substances that are not permitted to be mixed as a medicine. For example, preferably a purified PC-SOD having a specific SOD activity of 2,500 U/mg or more, and more preferably a purified PC-SOD having a specific SOD activity of 3,000 U/mg or more may be used as the PC-SOD.

In the present invention, 1 U (unit) represents an enzyme amount of PC-SOD that inhibits the NBT (nitro blue tetrazolium) reduction rate by 50% as measured using NBT under a condition of pH 7.8 and 30° C., in accordance with a method described in J. Biol. Chem., vol. 244, No. 22 6049-6055 (1969).

The agent for treating acute respiratory distress syndrome provided by the present invention is an agent for treating acute respiratory distress syndrome containing the PC-SOD thus prepared as an active ingredient, and may preferably be an agent for treating acute respiratory distress syndrome containing the PC-SOD and a stabilizing agent. Examples of the stabilizing agent may include a sugar component. The sugar component is not particularly limited as long as it can be used pharmaceutically; however sucrose is particularly preferable. Therefore, the most preferable agent for treating acute respiratory distress syndrome provided by the present invention is a composition containing PC-SOD and sucrose. As for sucrose, sucrose purified to such an extent that it may be used as a medicine is preferably used, and sucrose treated with activated carbon is particularly preferably used. The agent for treating acute respiratory distress syndrome can be prepared as a composition, in which use of such sucrose with PC-SOD can prevent reduction in the activity of the PC-SOD due to long team storage, the stability is high, and the property is particularly favorable even if it is lyophilized.

A mixing ratio of the PC-SOD to sucrose in the agent for treating acute respiratory distress syndrome of the present invention can be suitably determined depending on an administration amount, a form of the formulation, or the like, and is not particularly limited. However, a weight ratio of the PC-SOD to sucrose is preferably within a range of about 0.1:100 to 80:100, and more preferably about 0.4:100 to 60:100.

To the agent for treating acute respiratory distress syndrome of the present invention, another medical active component and a commonly-used formulation component such as an excipient, a binder, a lubricant, a colorant, a disintegrator, a buffer, a tonicity adjusting agent, a preservative, and a soothing agent can be added as long as they do not affect the activity of PC-SOD and the effect of the formulation.

The agent for treating acute respiratory distress syndrome provided by the present invention can be prepared using PC-SOD and sucrose by a commonly-used method that is pharmaceutically known. The PC-SOD used for a formulation composition of the present invention is preferably in a solution form, a frozen form, or a lyophilized form.

In one aspect, the agent for treating acute respiratory distress syndrome provided by the present invention may preferably be administered in the form of an injection. The injection is preferably in the form of solution, suspension, emulsion, or a solid formulation that is dissolved before use. These formulations can be prepared in accordance with a method described in General Rules for Preparations of The Japanese Pharmacopoeia.

In another aspect, the agent for treating acute respiratory distress syndrome provided by the present invention may preferably be administered in the form of an inhalant.

Such an inhalant means a pharmaceutical composition for delivery to the trachea, bronchus, lung, and the like, and is suitably a composition suitable for a nasal drop or administration through the nose or lung, and particularly a composition suitable for administration through the lung.

The inhalant can be produced in the form of powder, solution, or suspension using the above-described PC-SOD as an active ingredient.

When the inhalant is produced in a powder form, the above-described PC-SOD as an active ingredient may be pulverized as it is or with additives such as an excipient, a lubricant, a binder, a disintegrator, a stabilizing agent, or a corrective, to produce the inhalant.

When the inhalant is produced as a solution or suspension, for example, PC-SOD may be dissolved or suspended in water or a mixture of water and an auxiliary solvent, for example, an alcohol auxiliary solvent such as ethanol, propylene glycol, or polyethylene glycol, to produce the inhalant. Such a solution or suspension can additionally contain an antiseptic, a solubilizer, a buffer, a tonicity adjusting agent, an absorption promoter, a thickener, and the like.

The inhalant produced as described above is directly administered inside the nasal or mouth cavity or to the trachea, bronchus, lung, or the like by using common means in the field of inhalants, for example, a dropper, a pipette, a cannula, or a sprayer such as an atomizer or a nebulizer, the sprayer turning the inhalant into a nebulized form. In the case of using the sprayer, the inhalant can be administered by spraying it as an aerosol packaged in a pressurized container with an appropriate propellant (for example, gases of chlorofluorocarbons, such as dichlorofluoromethane, trichlorofluoromethane, or dichlorotetrafluoroethane, carbon dioxide, or the like), or by using a nebulizer.

The amount of PC-SOD that is an active ingredient in the agent for treating acute respiratory distress syndrome of the present invention and the administration amount of the formulation vary depending on a method for preparing the formulation, a dosage form, a target disease degree, or age or body weight of a patient and are not particularly limited. For example, an exemplary clinical amount can be 5 to 500 mg (15,000 to 1,500,000 U) per day per adult, and preferably, 40 to 200 mg (120,000 to 600,000 U) per day per adult. Further, the number of doses is not particularly limited, but the administration can be performed once or more daily.

EXAMPLES

Hereinafter, the present invention will be described in more detail by describing test examples that the present inventors specifically examined, instead of describing examples. However, the present invention is not limited to these descriptions.

<Materials and Methods>

LPS (lipopolysaccharide) is the one derived from *E. coli* and was purchased from Sigma-Aldrich Corporation (St. Louis, MO).

Diff-Quik was purchased from Sysmex Corporation (Kobe).

A DRI-CHEM slide (used for identification of BUN) was purchased from Fujifilm Corporation.

L-012 (luminescent probe), LabAssay creatinine, and Evans blue were purchased from Wako Pure Chemical Industries, Ltd.

Novo-Heparin (5000 units) was purchased from Mochida Pharmaceutical Co., Ltd.

Pentobarbital was purchased from Tokyo Chemical Industry Co., Ltd.

ICR mice (6 to 7-week old) were purchased from Charles River Laboratories, Inc.

<Cecal Ligation and Puncture Technique (CLP Technique)>

A mouse was anesthetized with pentobarbital (10 mg/kg, intraperitoneally) and a small abdominal midline incision was made to expose the cecum thereof. Subsequently, the cecum was ligated at approximately 2 cm with a silk thread and punctured twice with an 18 G needle (manufactured by Terumo Corporation). Then, the abdomen was closed.

Sham mice (sham operation group) were subjected to the same operation except the ligation and puncture of the cecum.

The survival rate was checked every 12 hours, and CLP-induced multiple organ failure was observed 8 hours after the CLP treatment.

<MV (Mechanical Ventilator) Technique in Mice>

A mechanical ventilator for small animals was used to induce ventilator-induced lung injury (VILI). After a mouse was anesthetized with pentobarbital (10 mg/kg, intraperitoneally), tracheotomy was performed and an 8 mm metal tube was inserted into the trachea thereof. The mouse was mechanically ventilated with a tidal volume of 17.5 mL/kg, a positive end-expiratory pressure of 0 cm $H_2O$, and a rate of 150 breaths/min.

Total respiratory elastance was measured every 30 minutes for 120 minutes by a snapshot technique.

The data were analyzed by using FlexiVent software (version 5.3 SCIREQ).

<Treatment of Mouse with Lipopolysaccharide (LPS), PC-SOD, and Other Drugs>

A mouse was anesthetized with isoflurane and 1 mg/kg LPS (in 0.9% NaCl) was administered thereto intratracheally once using a micropipette (P200). In the case of PC-SOD or dexamethasone, 3 or 15 KU/kg (1 or 5 mg/kg) of PC-SOD (in 0.45% NaCl) or 20 or 200 μg per mouse of dexamethasone (in 0.9% NaCl) was administered intravenously using a 26 G needle under isoflurane anesthesia. In the case of sivelestat, 10 or 100 mg/kg of sivelestat (in 0.9% NaCl) was administered intraperitoneally using a 21 G needle.

<Timing of Drug Administration>

The timing of the first drug administration after CLP, LPS, or MV procedure was immediately before the procedure for PC-SOD and dexamethasone, and 30 minutes before the procedure for sivelestat.

<Evaluation of Multiple Organ Failure and Systemic Inflammation>

For a quantitative examination of the permeability of an organ, Evans blue (EBD) (30 mg/kg) was administered to the mouse intravenously 2 hours before sacrificing the mouse. Tissue (lung, liver, and kidney) specimens were cut into pieces and incubated with a formaldehyde solution for 24 hours at 60° C. The specimens were centrifuged to obtain supernatants and the quantity of EBD was determined by using absorbance at 620 nm of the specimens.

Firstly, the wet weight of a lung was measured to determine a wet-to-dry weight ratio of the lung. Then, the lung was dried at 60° C. overnight and reweighed to obtain the dry weight thereof.

The levels of BUN and creatinine in blood were measured by using a DRI-CHEM slide and LabAssay creatinine, respectively, according to the protocols. The level of inflammatory cytokines in plasma was measured by an Elisa kit according to the protocol.

<Preparation of Bronchoalveolar Lavage Fluid (BALF)>

BALF was collected by inserting a cannula into a trachea and performing lavage twice with 1 mL of 50 U/mL heparin (in sterile 0.9% NaCl). Usually, about 1.8 mL of BALF was collected from each mouse. The amount of proteins in BALF was determined by a Bradford assay. The level of inflammatory cytokines was determined by the Elisa kit as described above.

<Measurement of Reactive Oxygen Species by In Vivo Imaging Analysis>

Measurement of reactive oxygen species (ROS) in a mouse was performed by in vivo imaging analysis with some modifications.

An imaging system (Lumazone, in vivo imaging system, SHOSHIN EM, Okazaki, Japan) including a chamber equipped with an electron multiplying CCD camera was used. L-012 (in saline), which is a luminescent probe, was administered to the mouse intravenously at 75 mg/kg.

In the case of the CLP model, the mouse was euthanized 2 minutes after injection of L-012, subjected to abdominal midline incision, and imaged (five-minute intervals).

In the case of the LPS and MV models, the mouse was euthanized 5 minutes after injection of L-012, and the lung thereof was anatomized promptly and imaged (five-minute intervals).

The data were analyzed by using SlideBook6 software (Intelligent Imaging Innovations, Inc., Denver, CO).

<Histopathological Analysis>

A tissue specimen was fixed in 10% neutral buffered formalin for 24 hours and then embedded in paraffin before being cut into a section 4 μm thick. The section was stained firstly with Mayer's hematoxylin and secondly with 1% alcoholic eosin solution (H&E staining). The specimen was mounted with malinol (mounting medium) and scanned using a NanoZoomer-XR digital slide scanner (Hamamatsu Photonics K.K.).

All the scanned images were analyzed using NDP-view2 software (Hamamatsu Photonics K.K.) and Image J software.

The results of the aforementioned tests are described below with reference to the results shown in the diagrams.

Test 1: Evaluation of Effect of PC-SOD on Survival Rate of Mice Subjected to Cecal Ligation and Puncture Technique (CLP Technique)

Male ICR mice were subjected to a CLP technique and PC-SOD (kU/kg) or vehicle was administered thereto.

The results were shown in FIG. 1.

(A) in the diagram shows the results when administration was performed immediately before the CLP operation and 12, 24, and 48 hours after the CLP operation.

(B) in the diagram shows the results when administration was performed 1, 12, 24, and 48 hours after the CLP operation.

The following was found from both the results: PC-SOD administration (immediately before the CLP operation and 1, 24, and 48 hours after the CLP operation) increased the survival rate in a dose-dependent manner (Results A).

PC-SOD administration (1, 24, and 48 hours after the CLP operation) also increased the survival rate (Results B).

Test 2: Evaluation of Effect of PC-SOD and Other Drugs on CLP-Induced Multiple Organ Failure A CLP operation or a sham operation was performed on male ICR mice.

Drugs were administered once before the CLP operation or the sham operation. PC-SOD (kU/kg) and dexamethasone (μg/mouse) were intravenously administered. Sivelestat (mg/kg) was intraperitoneally administered. EBD (Evans blue dye) (30 mg/kg) was administered intravenously 6 hours after the CLP operation. Two hours later, EBD was extracted from the kidney and liver and measured.

Furthermore, plasma samples were prepared 8 hours after the CLP operation and the levels of BUN and creatinine were measured.

The results were shown in FIG. 2.

(A) in the diagram shows the results of intravenous administration of PC-SOD and demonstrates that PC-SOD administration suppressed an increase in vascular permeability caused by CLP (kidney and liver).

(B) in the diagram shows the results of intravenous administration of PC-SOD and demonstrates that PC-SOD administration suppressed an increase of BUN (blood urea nitrogen) and creatinine (indicator of kidney function) caused by CLP.

(C) and (D) in the diagram show the results of administration of dexamethasone and sivelestat. As is found from the results shown therein, an increase of BUN and creatinine caused by CLP was not suppressed by administrating a currently clinically used steroid (dexamethasone: Dex) or sivelestat (Siv).

The results as above provide a better understanding of specificity of the effect of PC-SOD of the present invention, which is different from that of the steroid (dexamethasone) or sivelestat.

Test 3: Evaluation of Effect of PC-SOD and Other Drugs on CLP-Induced Systemic Inflammation A CLP operation or a sham operation was performed on male ICR mice.

Drugs were administered once before the CLP operation or the sham operation. PC-SOD (kU/kg) and dexamethasone (μg/mouse) were intravenously administered. Sivelestat (mg/kg) was intraperitoneally administered. EBD (Evans blue dye) (30 mg/kg) was administered intravenously 8 hours after the CLP operation. Plasma samples were prepared and the level of inflammatory cytokines in plasma was measured.

The results were shown in FIG. 3.

(A) in the diagram shows the results of intravenous administration of PC-SOD and demonstrates that PC-SOD administration suppressed an increase of TNF-α and IL-6, which are inflammatory cytokines, caused by CLP.

In contrast, (B) and (C) in the diagram show the results of administration of dexamethasone (Dex) and sivelestat (Siv) and demonstrate that administration thereof failed in suppressing an increase of TNF-α and IL-6.

The results as above also provide a better understanding of specificity of the effect of PC-SOD of the present invention, which is different from that of the steroid (dexamethasone) or sivelestat.

Test 4: Evaluation of Effect of PC-SOD on Lipopolysaccharide (LPS)-Induced Lung Injury LPS (1 mg/kg) or vehicle (control) was administered once into a trachea of a male ICR mouse.

PC-SOD (kU/kg) or vehicle was administered intravenously once immediately before the administration of lipopolysaccharide (LPS). ESD (Evans blue dye) (30 mg/kg) was injected intravenously 6 hours after a CLP operation. Two hours later, ESD was extracted from the lung and liver and the amount thereof was measured (Test A).

A section of the lung tissue was prepared 24 hours after the LPS administration and was subjected to a histopathological examination (H&E staining) (Test B). The lesion area was determined by ImageJ software (Test C). BALF was prepared 48 hours after the LPS administration and the levels of protein (Test D) and inflammatory cytokines (Test E) were determined.

These results were shown in FIGS. 4.1 and 4.2. Each of (A) to (E) in the diagram shows each result of Tests A to E.

As is found from the results shown in (A) in the diagram, PC-SOD administration suppressed an increase in vascular permeability caused by lipopolysaccharide (LPS) (lung and liver).

The results shown in (B) in the diagram demonstrated that PC-SOD administration suppressed alveolar hemorrhage, leukocyte infiltration, and lung interstitial edema caused by lipopolysaccharide (LPS).

Furthermore, as is found from the results shown in (C) in the diagram, PC-SOD administration reduced a lung disorder area caused by lipopolysaccharide (LPS).

Furthermore, as is shown in (D) in the diagram, PC-SOD administration suppressed an increase of protein in the BALF (bronchoalveolar lavage fluid) (this increase indicates lung injury and edema) caused by lipopolysaccharide (LPS). The results shown in (E) in the diagram demonstrated that PC-SOD suppressed an increase of TNF-$\alpha$, IL-10, and IL-6 (inflammatory cytokines) in the BALF (bronchoalveolar lavage fluid) caused by lipopolysaccharide (LPS).

Test 5: Effect of PC-SOD on Mechanical Ventilator (MV)-Induced Lung Injury and Change of Lung Mechanics Male ICR mice were subjected to MV (mechanical ventilator) treatment or were not subjected to MV treatment (control).

PC-SOD (15 kU/kg) or vehicle was administered intravenously once immediately before the MV treatment. EBD (Evans blue dye) (30 mg/kg) was simultaneously administered intravenously, extracted from the lung 2 hours after the MV treatment, and measured (Test A).

The wet-to-dry weight ratio of the lung was determined 2 hours after the MV treatment (Test B).

A section of the lung tissue was prepared 2 hours after the MV treatment and was subjected to a histopathological examination (H&E staining) (Test C).

The lesion area was determined by ImageJ software (Test D).

Total respiratory elastance was measured every 30 minutes for 120 minutes (Test E).

These results were shown in FIGS. 5.1 and 5.2. Each of (A) to (E) in the diagram shows each result of Tests A to E.

The results shown in (A) in the diagram shows that PC-SOD administration suppressed an increase in vascular permeability caused by MV (lung).

The results shown in (B) also showed that PC-SOD administration suppressed lung edema caused by MV.

Furthermore, as is clear from the results shown in (C) and (D) in the diagram, PC-SOD administration suppressed lung injury caused by MV. As is found from the results of (E), PC-SOD administration suppressed an increase in lung elastance caused by MV.

Test 6: Effect of Dexamethasone and Sivelestat on Mechanical Ventilator (MV)-Induced Lung Injury and Change of Lung Mechanics (Comparative Examination)

Male ICR mice were subjected to MV treatment or were not subjected to MV treatment (control), as with the above-mentioned Test 5.

Dexamethasone (Dex) (200 µg/mouse) or vehicle was administered intravenously once immediately before the MV treatment.

Sivelestat (Siv) (100 mg/kg) or vehicle was administered intraperitoneally once immediately before the MV treatment.

The wet-to-dry weight ratio of the lung was determined 2 hours after the MV treatment (Tests A and C). Total respiratory elastance was measured every 30 minutes for 120 minutes (Tests B and D).

The results were shown in FIG. 6. Each of (A) to (D) in the diagram shows each result of Tests A to D.

As is found from the results shown in (A) and (C) in the diagram, lung edema caused by MV was not suppressed by administration of a steroid (dexamethasone: Dex) or sivelestat (Siv).

Furthermore, as is found from the results shown in (B) and (D) in the diagram, increase of lung elastance caused by MV was not suppressed by administration of the steroid (dexamethasone: Dex) or sivelestat (Siv), either.

Test 7: Evaluation of Effect of PC-SOD on Level of Reactive Oxygen Species (ROS) In Vivo CLP operation (Tests A and B), LPS administration (Tests C and D), and MV treatment (Tests E and F) were performed as described above. As described above, PC-SOD (3 or 15 kU/kg) was administered intravenously once before the CLP operation, LPS administration, or MV treatment. A luminescent probe (L-012) (75 mg/kg) was administered 4 hours after the CLP operation, 6 hours after the LPS administration, and 2 hours after the MV treatment. An abdominal cavity (Test A) or a lung (Tests C and E) of the mouse was imaged using a Lumazone in vivo imaging system. The sum intensity of reactive oxygen species (ROS) was determined by Slide Book6 software (Tests B, D, and F).

The results were shown in FIGS. 7.1 to 7.3. Each of (A) to (F) in the diagram shows each result of Tests A to F.

As is also clear from the results of Test B shown in (B) in the diagram, PC-SOD administration suppressed an increase of reactive oxygen species in the abdominal cavity caused by the CLP operation.

PC-SOD administration also suppressed an increase of reactive oxygen species in the lung caused by lipopolysaccharide (LPS) as well as an increase of reactive oxygen species in the lung caused by the mechanical ventilator (MV).

These results were also supported by the results of imaging of the inside of murine abdominal cavity shown in (A) in the diagram (Test A) or the lung shown in (C) and (E) in the diagram (Tests C and E), the imaging using the Lumazone in vivo imaging system.

Test 8: Effect of Dexamethasone or Sivelestat on Level of Reactive Oxygen Species (ROS) In Vivo (Comparative Examination)

As a comparative test to Test 7, effects of dexamethasone (Dex) and sivelestat (Siv) were evaluated.

Male ICR mice were subjected to a CLP operation. Dexamethasone (200 μg/mouse) was administered intravenously once before the CLP operation (Tests A and C). Sivelestat (100 mg/kg) was administered intraperitoneally (Tests B and D). A luminescent probe (L-012) (75 mg/kg) was administered 4 hours after the CLP operation in each test. An abdominal cavity of the mouse was imaged using a Lumazone in vivo imaging system (Tests A and B). The sum intensity of ROS was determined by SlideBook6 software (Tests C and D).

The results were shown in FIG. 8. Each of (A) to (D) in the figure shows each result of Tests A to D.

As is also clear from the results shown in (C) and (D) in the diagram, increase of reactive oxygen species caused by the cecal ligation and puncture technique (CLP) was not suppressed by administration of a steroid (dexamethasone) or sivelestat.

These facts were also found by imaging the abdominal cavity of the mouse using the Lumazone in vivo imaging system as shown in (A) and (B) in the diagram.

Judging from the above, an increase of reactive oxygen species in ARDS may not be suppressed by the steroid (dexamethasone) or sivelestat but was significantly suppressed by PC-SOD of the present invention. This finding provides a better understanding of the specificity of the present invention.

Test 9: Evaluation of Effect of Heat-Inactivated PC-SOD on CLP-Induced Renal Dysfunction and Systemic Inflammation The effect of heat-inactivated PC-SOD was evaluated to confirm the effect of PC-SOD of the present invention.

PC-SOD solution was heated at 100° C. for 60 minutes for inactivation.

A CLP operation or a sham operation was performed on a male ICR mouse. The heat-inactivated PC-SOD (kU/kg; kU before heat-inactivation) was administered intravenously once before the CLP operation. A plasma sample was prepared 8 hours after the CLP investigation and the levels of BUN and creatinine (Test A) and the level of inflammatory cytokines (Test B) were measured.

The results were shown in FIG. 9.

As is found from the results shown as (A) and (B) in the diagram, an increase of BUN and creatinine, and TNF-α and IL-6 caused by CLP was not suppressed by the heat-inactivated PC-SOD (Heat-PC).

Test 10: Evaluation of Effect of NAC (N-Acetyl Cysteine) or Unmodified SOD on CLP-Induced Renal Dysfunction and Systemic Inflammation As with Test Example 9, the effect of NAC (N-acetyl cysteine) or unmodified SOD was evaluated to confirm the effect of PC-SOD of the present invention.

A CLP operation or a sham operation was performed on a male ICR mouse. NAC (mg/kg) was administered intraperitoneally or unmodified SOD (kU/kg) was administered intravenously, once before the CLP operation. A plasma sample was prepared 8 hours after the CLP operation and the levels of BUN and creatinine (Test A) and the level of inflammatory cytokines (Test B) were measured.

The results were shown in FIG. 10.

As is found from the results shown as (A) and (B) in the diagram, an increase of BUN and creatinine, and TNF-α and IL-6 caused by CLP was not suppressed by NAC or unmodified SOD.

Judging from the results of Test Examples 9 and 10 as above, it is understood that PC-SOD of the present invention is specific for CLP-induced renal dysfunction and systemic inflammation.

The results of the aforementioned test examples suggested that PC-SOD of the present invention is beneficial to acute respiratory distress syndrome (ARDS) patients.

Currently, there is no therapeutic drug that ameliorates ARDS (acute respiratory distress syndrome) distinctly. Therefore, a mechanical ventilator (MV: mechanical ventilation) is used for critical care, however, mechanical ventilator involves a high tidal volume and causes ventilator-induced lung injury (VILI), making the mortality rate of ARDS high.

Reactive oxygen species (ROS) such as a superoxide anion contributes to onset of ARDS or VILI. SOD (superoxide dismutase) catalyzes dismutation of the superoxide anion. However, the clinical effect of SOD has fallen short of our expectations because of the low affinity to tissue and low stability in blood plasma (plasma) thereof.

As is found from the test examples described above, PC-SOD provided by the present invention is found to be very effective in mice against the cecal ligation and puncture technique (CLP) (a peritonitis model) or administration of lipopolysaccharide (LPS), or MV-induced tissue damage (mechanical ventilator-induced tissue damage), edema, or inflammation in the lung.

Furthermore, intravenous administration of PC-SOD increased the survival rate and reduced the vascular permeability in the mice treated by the CLP technique, and suppressed CLP-induced inflammation of the whole body as well as the kidney in contrast to dexamethasone or sivelestat.

In particular, although administration of lipopolysaccharide (LPS) induces vascular permeability, tissue injury, and inflammation in the lung, all of these induced symptoms were suppressed by administration of PC-SOD.

Furthermore, all of the vascular permeability, edema, tissue injury, and a mechanical change in the lung induced by MV were suppressed by PC-SOD, but not by dexamethasone or sivelestat.

Furthermore, according to the in vivo imaging analysis of ROS (reactive oxygen species) resulting from the CLP operation and LPS administration, and MV, the level of ROS (reactive oxygen species) was increased and the increase was suppressed by administration of PC-SOD but not by dexamethasone or sivelestat.

These results suggest that intravenous administration of PC-SOD is beneficial to ARDS patients.

Formulation Example 1: Intravenous Injection

1% (w/w) of PC-SOD, 10% (w/w) of sucrose, and 0.05% (w/w) of benzalkonium chloride were dissolved in an aqueous solution of 5% xylitol, and the solution was lyophilized. To the obtained lyophilized product, 0.5% carmellose that was separately filled in a vial or water for injection was added, to obtain an intravenous injection.

Example 2: Inhalant

Liquid Formulation for Inhalation (1)

1% (w/w) of PC-SOD, 10% (w/w) of sucrose, and 0.05% (w/w) of benzalkonium chloride were dissolved in an aqueous solution of 5% xylitol, to prepare a liquid formulation for inhalation.

Liquid Formulation for Inhalation (2)

1% (w/w) of PC-SOD, 10% (w/w) of sucrose, 0.05% (w/w) of benzalkonium chloride, 10% (w/w) of polyethylene glycol, 20% (w/w) of propylene glycol, and purified water making up the balance were used to prepare a liquid formulation for inhalation.

Powder Formulation for Inhalation

5% (w/w) of PC-SOD and sucrose making up the balance (fine powder) were used to prepare a powder formulation for inhalation.

INDUSTRIAL APPLICABILITY

As described above, an agent for ameliorating acute respiratory distress syndrome provided by the present invention contains a specific PC-SOD as an active ingredient, and has a higher affinity for, for example, cell membranes than a conventional SOD and a greater ability to eliminate superoxide anions in a lesion.

Therefore, the present invention provides an agent for treating acute respiratory distress syndrome that contains PC-SOD as an active ingredient. This agent is effective against edema, a tissue injury, and inflammation in a lung and other organs that neither a steroid nor sivelestat was effective against, and thus brings new hope to treatment of ARDS and VILI and has a great value in medical care.

The invention claimed is:

1. A method for treating multiple organ failure accompanied by systemic inflammation, the method consisting of:

administering an active agent consisting of a lecithinized superoxide dismutase, and a stabilizing agent, the lecithinized superoxide dismutase being represented by the following general formula (I):

SOD'(Q-B)m (I)

wherein,

SOD' represents a residue of a superoxide dismutase;

Q represents a chemical crosslinking;

B represents a residue of lysolecithin, in which a hydrogen atom of a hydroxyl group is removed from the lysolecithin having the hydroxyl group at the 2-position of glycerol; and m is the average number of bonds of the lysolecithin relative to one molecule of the superoxide dismutase and represents an integer of 1 or more, wherein the multiple organ failure is associated with organs consisting of kidney and liver, and wherein the administering of the active agent and the stabilizing agent occurs via inhalation or intravenous injection.

2. The method according to claim 1, wherein Q in the formula (I) is —C—(O)—(CH2)n-C(O)—, wherein, n represents an integer of 2 or more.

3. The method according to claim 1, wherein SOD' is a residue of a human superoxide dismutase.

4. The method according to claim 1, wherein SOD' is a residue of a modified superoxide dismutase in which an amino acid at a 111-position in an amino acid sequence of a human superoxide dismutase is converted into S-(2-hydroxyethylthio) cysteine.

5. The method according to claim 3, wherein the superoxide dismutase is a superoxide dismutase containing copper and zinc in an active center thereof.

6. The method according to claim 1, wherein n is an integer of 2 to 10.

7. The method according to claim 1, wherein m is an integer of 1 to 12.

8. The method according to claim 1, wherein the stabilizing agent is a sugar.

9. The method according to claim 8, wherein the sugar is sucrose.

10. The method according to claim 9, wherein the sucrose is sucrose treated with activated carbon.

* * * * *